US010596391B2

(12) United States Patent
Willcut

(10) Patent No.: US 10,596,391 B2
(45) Date of Patent: Mar. 24, 2020

(54) SYSTEMS AND METHODS OF ACCOUNTING FOR SHAPE CHANGE DURING RADIOTHERAPY

(71) Applicant: Elekta, Inc., Atlanta, GA (US)

(72) Inventor: Virgil Willcut, Maryland Heights, MO (US)

(73) Assignee: Elekta, Inc., Atlanta, GA (US)

( * ) Notice: Subject to any disclaimer, the term of this patent is extended or adjusted under 35 U.S.C. 154(b) by 122 days.

(21) Appl. No.: 15/839,381

(22) Filed: Dec. 12, 2017

(65) Prior Publication Data
US 2018/0326223 A1    Nov. 15, 2018

Related U.S. Application Data

(60) Provisional application No. 62/504,926, filed on May 11, 2017.

(51) Int. Cl.
*A61N 5/10*    (2006.01)

(52) U.S. Cl.
CPC .......... *A61N 5/1037* (2013.01); *A61N 5/107* (2013.01); *A61N 5/1039* (2013.01); *A61N 5/1045* (2013.01); *A61N 5/1031* (2013.01); *A61N 2005/1052* (2013.01); *A61N 2005/1055* (2013.01); *A61N 2005/1061* (2013.01)

(58) Field of Classification Search
CPC .. A61N 5/1037; A61N 5/1039; A61N 5/1045; A61N 5/107
See application file for complete search history.

(56) References Cited

U.S. PATENT DOCUMENTS

2014/0161339 A1* 6/2014 Wakai ................... G06T 7/0012
                                                       382/131
2015/0165235 A1    6/2015 Fujisawa

FOREIGN PATENT DOCUMENTS

WO    WO-2012058615 A1    5/2012
WO    WO-2018208390 A1    11/2018

OTHER PUBLICATIONS

"International Application Serial No. PCT/US2018/026199, International Search Report dated Jul. 5, 2018", 5 pgs.
"International Application Serial No. PCT/US2018/026199, Written Opinion dated Jul. 5, 2018", 5 pgs.
(Continued)

*Primary Examiner* — Utpal D Shah
(74) *Attorney, Agent, or Firm* — Schwegman Lundberg & Woessner, P.A.; Sanjay Agrawal

(57) ABSTRACT

Embodiments of the disclosure may be directed to a system for generating a motion target volume representative of shape changes of a target region in a patient. The system may comprise at least one computer system configured to receive a plurality of electronic medical images that include the target region, and each of the plurality of images may have been taken at a different time point. The computer system may be configured to define a three-dimensional volume containing the target region in each of the plurality of images, and the three-dimensional volume may be different in at least two of the plurality of images due to differences in shape of the target region in the at least two images. The computer system may also be configured to co-register the three-dimensional volumes and generate the motion target volume, wherein the motion target volume encompasses each of the three-dimensional volumes.

24 Claims, 13 Drawing Sheets

(56) References Cited

OTHER PUBLICATIONS

Ikuno, Nishibuchi, et al., "Time-Adjusted Internal Target Volume: A Novel Approach Focusing on Heterogeneity of Tumor Motion Based on 4-Dimensional Computed Tomography Imaging for Radiation Therapy Planning of Lung Cancer", International Journal of Radiation:Oncology Biology Physics, vol. 89, No. 5, (Jul. 8, 2014), 1129-1137.

"International Application Serial No. PCT/US2018/026199, International Preliminary Report on Patentability dated Nov. 21, 2019", 7 pgs.

* cited by examiner

SYSTEMS AND METHODS OF ACCOUNTING FOR SHAPE CHANGE DURING RADIOTHERAPY

CROSS-REFERENCE TO RELATED APPLICATIONS

This application claims the benefit of U.S. Provisional Application No. 62/504,926, filed May 11, 2017, the disclosure of which is incorporated herein by reference in its entirety.

TECHNICAL FIELD

Aspects of the present disclosure relate generally to radiotherapy, and, specifically, to methods and systems for determining and accounting for changes in shape of a target volume, e.g., a tumor, during radiotherapy.

BACKGROUND

Radiation therapy (also referred to as radiotherapy) may be used in the treatment of cancer or other pathologies. Radiotherapy involves delivering a prescribed dose of radiation to a target region of a patient, for example, to a tumor or other cancerous tissue. The target region may be imaged prior to the administration of radiotherapy, and a radiotherapy treatment plan ("treatment plan") may be formulated based on, e.g., the shape, size, location, and/or orientation of the target and the surrounding structures, among other things. A radiotherapy delivery device may then be used to deliver radiation to the target region of the patient, in accordance with the treatment plan.

Traditionally, for each patient, a treatment plan may be created based on clinical and dosimetric objectives and constraints (e.g., the maximum, minimum, and mean doses of radiation to the tumor and surrounding organs). The treatment planning procedure may include using a three-dimensional (3D) image of the patient to identify a target region (e.g., the tumor) and to identify critical organs near the tumor.

After initial images of the target are acquired, however, the shape of the target region may change. For example, a patient may move voluntarily or involuntarily due to regular biological processes, including, e.g., breathing, swallowing, blinking, twitching, peristalsis, digestion, filling of the bladder, beating of the heart, or other movements. These movements may compress and/or otherwise deform or re-shape the target region. While systems exist for tracking the movement of a target region, this tracking generally only accounts for changes in the location of a target region in the body. Current systems assume a constant shape of the target region during the movement being tracked, i.e., they assume that the target region is rigid. Often, however, tumors or other cancerous growths are formed of soft tissue and may be deformed by normal body processes. Currently available systems may not be able to track changes to the actual shape of the target region that may occur between treatment planning and radiotherapy or during radiotherapy.

Changes in the shape of the target region that are not accounted for may reduce the efficacy of radiotherapy. For example, if the shape of the target region is different than the assumed shape based on prior imaging, then an incorrect dose of radiation may be delivered to the intended target region or portions of the target region may be missed entirely. Additionally, surrounding healthy structures may receive radiation instead of, or in addition to, the intended target region. Exposing the wrong area to radiation may ultimately harm or kill surrounding healthy cells. Accordingly, there is a need for systems and methods capable of accounting for variations in the shape of a target region during radiotherapy. There is a need for systems and methods of generating a motion target volume for use during radiotherapy that accounts for changes in the shape of the target region when tracking the delivery of radiation.

SUMMARY

Embodiments of the disclosure may be directed to a system for generating a motion target volume representative of shape changes of a target region in a patient. The system may include at least one computer system configured to receive, among other things, a plurality of electronic medical images that include the target region, and each of the plurality of images may have been taken at a different time point. The computer system may be configured to define a three-dimensional volume containing the target region in each of the plurality of images, and the three-dimensional volume may be different in at least two of the plurality of images due to differences in shape of the target region in the at least two images. The computer system may also be configured to co-register the three-dimensional volumes and generate the motion target volume, wherein the motion target volume encompasses each of the three-dimensional volumes.

Various embodiments of the system may include one or more of the following features: the co-registering may occur before the defining, or the three-dimensional volume may be a gross tumor volume; the at least one computer system may be further configured to define a first margin around each of the three-dimensional volumes, wherein the first margin defines a clinical target volume, and the at least one computer system may be further configured to define a second margin around each of the first margins, wherein the second margin defines a planning target volume; the at least one computer system may be configured to define a first margin around the co-registered three-dimensional volumes, wherein the first margin defines a clinical target volume, and may be configured to define a second margin around the first margin, wherein the second margin defines a planning treatment volume; and the plurality of images may include at least one of a magnetic resonance image or a computed tomography image.

Embodiments of the present disclosure may also be drawn to a computer-implemented method for generating a motion target volume representative of changes in shape of a target region within a body of a patient. The method may include receiving a plurality of medical images that include the target region within the body of the patient, wherein each of the plurality of images was taken at a different time point, and contouring a three-dimensional target volume containing the target region in at least one of the plurality of images. The method may also include co-registering the plurality of images in a region around the three-dimensional target volume, and generating the motion target volume, wherein the motion target volume encompasses a shape of the target region in each of the plurality of images.

Various embodiments of the system may include one or more of the following features: the contouring may comprise contouring a three-dimensional target volume containing the target region in each of the plurality of images; the contouring may be performed on one of the plurality of images, and the method may further comprise propagating the target volume from the one of the plurality of images onto the target region in another of the plurality of images; the method may further comprise creating a maximum intensity projection or a minimum intensity projection; a margin may be added around the minimum intensity projection or the maximum intensity projection to create a clinical target volume, a margin may be added around the clinical target volume to create a planning target volume, or the contouring may include adding a margin around the three-dimensional volume, wherein the three-dimensional volume includes a tumor; and the method may also comprise creating a region of interest to guide the co-registration.

Embodiments of the present disclosure may also be drawn to a computer-implemented method for generating a motion target volume representative of changes in shape of a target region within a body of a patient. The method may include receiving a plurality of medical images that include the target region within the body of the patient, wherein each of the plurality of images was taken at a different time point. The method may also include defining a region of interest for co-registration in at least one of the plurality of images, co-registering the plurality of images in the region of interest, and creating a maximum intensity projection or a minimum intensity projection for generation of the motion target volume.

Various embodiments of the system may include one or more of the following features: a region of interest for co-registration may be defined in each of the plurality of images, or the region of interest may be a gross tumor volume; the method may further comprise adding a first margin around the maximum intensity projection or the minimum intensity projection, and the first margin may define a clinical target volume; and the method may further comprise adding a second margin around the clinical target volume, wherein the second margin defines a planning target volume.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings.

DETAILED DESCRIPTION

Figure 1:
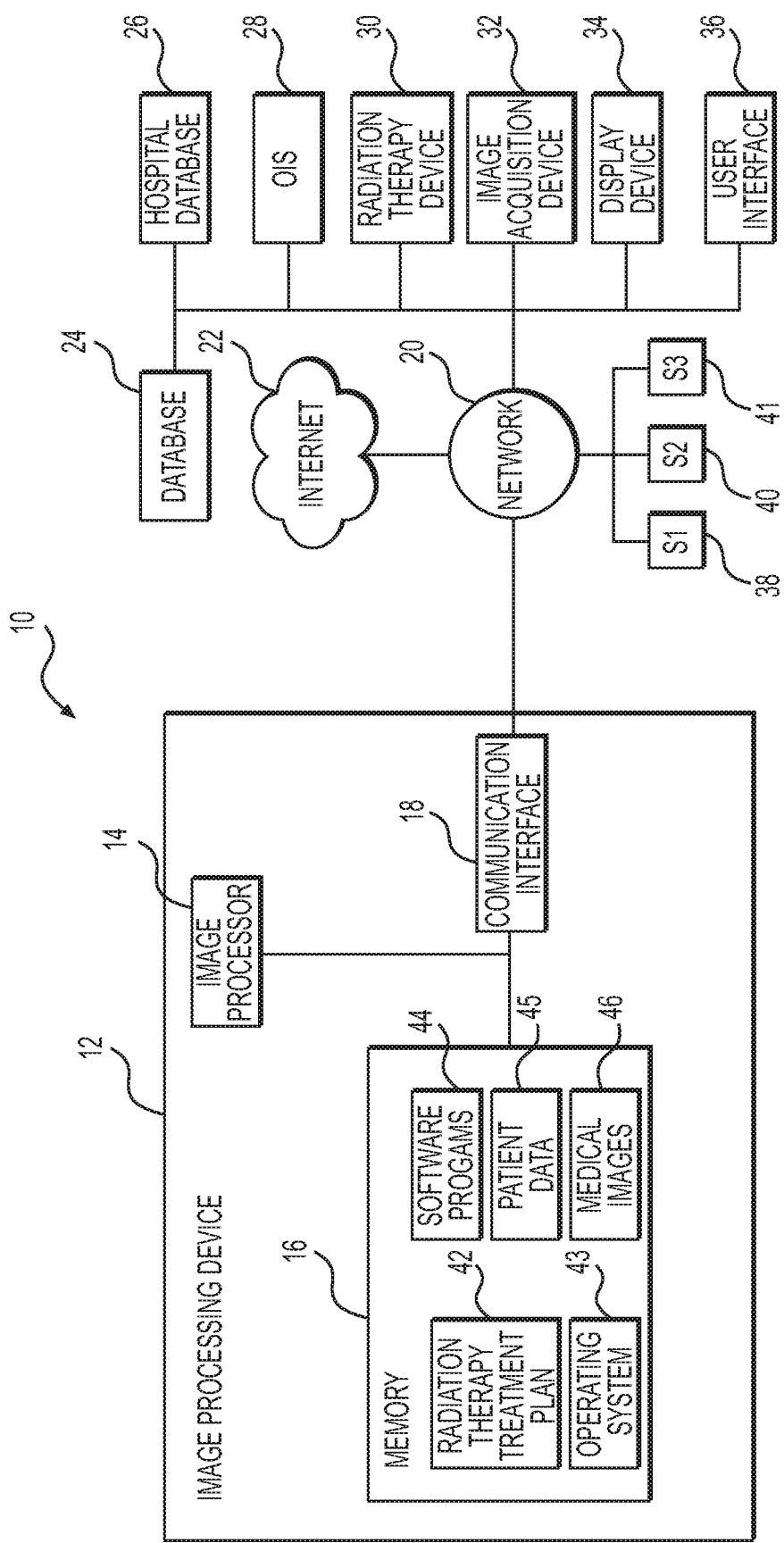
FIG. 1 illustrates an example of a radiotherapy system.

Reference will now be made in detail to the exemplary embodiments of the present disclosure described below and illustrated in the accompanying drawings. Wherever possible, the same reference numbers will be used throughout the drawings to refer to same or like parts. The term "exemplary" is used in the sense of "example," rather than "ideal." The term "approximately" is used to mean within a range of 10% of the number it modifies.

Embodiments of this disclosure are drawn to radiotherapy systems and methods for creating graphical representations that account for and encompass changes in shape of a target region (e.g., a tumor) during radiotherapy. For example, systems and methods described herein may be used to create a motion target volume for use with radiotherapy treatment planning and/or for use with tumor tracking for motion management. Many ways of generating a motion target volume that accounts for changes in shape are described herein. For example, a plurality of medical images depicting various changes in shape may be acquired or may have previously been acquired. The plurality of images, or a subset of the images, may be processed in order to generate a motion target volume to account for changes in tumor shape.

In particular, during treatment planning, a plurality of medical images, for example, computed tomography (CT) images, magnetic resonance images (MRI—e.g., 3D or 4D MRI images), ultrasound images, fluoroscopy, X-ray images, positron emission tomography (PET), and/or other suitable medical imaging may be taken. The location of a target region, for example, a tumor in the anatomy of the patient, may be determined by the radiotherapy system using segmentation techniques, or other configurations, known in the art. Because the images may be taken at different time points, the shape of the target region may vary in different images. For example, changes in the shape of the target region may vary in response to respiration or digestion. The shape of the target region may be compressed, expanded, deformed, or otherwise distorted during treatment planning, between treatment planning and radiotherapy, and/or during radiotherapy. Embodiments of the present disclosure may allow for these changes in shape to be taken into account during radiotherapy and/or when generating a motion target volume.

As used herein, the term "gross tumor volume" (GTV) refers to the visible extent of a tumor. The term "clinical target volume" (CTV) refers to the gross tumor volume, plus a margin to account for sub-clinical disease that may be present but not visible in medical imaging. The CTV surrounds the GTV and represents the extent of undetected spreading of the tumor and should also be addressed in order to appropriately treat the tumor. The term "planning target volume" (PTV) refers to the CTV, plus a margin to account for uncertainty introduced in the panning stages and/or during the delivery of treatment to the patient (e.g., radiotherapy). The PTV surrounds the CTV and is designed to promote the actual delivery of treatment to the CTV. The term "target volume" broadly encompasses each of these terms, and the "motion target volume" refers to a target volume used for tracking motion of the tumor during the delivery of radiotherapy to the patient. A "region of interest" generally refers to an area of the body, which may include one or more of the GTV, CTV, and/or PTV, or even additional portions of the body outside of the target volumes.

FIG. 1 illustrates another exemplary radiotherapy system 10 for providing radiation therapy to a patient with which embodiments of the disclosure may be used and/or executed. Radiotherapy system 10 includes an image processing device 12. Image processing device 12 may be connected to a network 20. Network 20 may be connected to Internet 22. Network 20 may connect image processing device 12 with one or more of a database 24, a hospital database 26, an oncology information system (OIS) 28, a radiation therapy device 30, an image acquisition device 32, a display device 34, and/or a user interface 36. Image processing device 12 may be configured to generate one or more radiation therapy treatment plans 42 to be used by radiation therapy device 30.

Image processing device 12 may include a memory 16, an image processor 14, and/or a communication interface 18. Memory 16 may store computer-executable instructions, such as an operating system 43, one or more radiation therapy treatment plans 42 (e.g., original treatment plans, and/or adapted treatment plans), software programs 44 (e.g., artificial intelligence, deep learning, neural networks, and/or radiotherapy treatment plan software), and/or any other computer-executable instructions to be executed by image processor 14. In some embodiments, software programs 44 may convert medical images of one format (e.g., MRI) to another format (e.g., CT) by producing synthetic images, such as a pseudo-CT image. For instance, software programs 44 may include image processing programs to train a predictive model for converting a medial image 46 in one modality (e.g., an MR image) into a synthetic image of a different modality (e.g., a pseudo CT image); alternatively, the trained predictive model may convert a CT image into an MRI image. Memory 16 may store data, including medical images 46, patient data 45, and/or other data required to create and/or implement radiation therapy treatment plan 42.

In addition to, or instead of, memory 16 storing software programs 44, it is contemplated that software programs 44 may be stored on a removable computer medium, such as a hard drive, a computer disk, a CD-ROM, a DVD, an HD, a Blu-Ray DVD, a USB flash drive, an SD card, a memory stick, or any other suitable medium. Software programs 44, when downloaded to image processor 14, may be executed by image processor 14.

Image processor 14 may be communicatively coupled to memory 16, and image processor 14 may be configured to execute computer-executable instructions stored thereon. Image processor 14 may send or receive medical images 46 to memory 16. For example, image processor 14 may receive medical images 46 from image acquisition device 32, or another image acquisition device, via communication interface 18 and network 18 to be stored in memory 16. Image processor 14 may also send medical images 46 stored in memory 16 via communication interface 18 to network 20 be stored in database 24 and/or hospital database 26.

Further, image processor 14 may utilize software programs 44 (e.g., treatment planning software) along with medical images 46 and/or patient data 45 to create and/or modify radiation therapy treatment plan 42. Medical images 46 may include information such as imaging data associated with a patient anatomical region, organ, or volume of interest segmentation data. Patient data 45 may include information such as (1) functional organ modeling data (e.g., serial versus parallel organs, appropriate dose response models, etc.); (2) radiation dosage data (e.g., dose-volume histogram (DVH) information); and/or (3) other clinical information about the patient and course of treatment (e.g., other surgeries, chemotherapy, previous radiotherapy, etc.).

In addition, image processor 14 may utilize software programs to generate intermediate data, such as updated parameters to be used, for example, by a neural network model, or to generate an intermediate 2D or 3D image, which may then subsequently be stored in memory 16. Image processor 14 may then transmit executable radiation therapy treatment plan 42 via communication interface 18 to network 20 to radiation therapy device 30, which may execute radiation therapy treatment plan 42 to treat a patient with radiation. In addition, image processor 14 may execute software programs 44 to implement functions, such as, e.g., image conversion, image segmentation, deep learning, neural networks, and/or artificial intelligence. For instance, image processor 14 may execute software programs 44 that train and/or contour a medical image. Such software programs 44, when executed, may train a boundary detector and/or utilize a shape dictionary.

Image processor 14 may be a processing device, include one or more general-purpose processing devices such as a microprocessor, a central processing unit (CPU), a graphics processing unit (GPU), and/or an accelerated processing unit (APU), for example. More particularly, in some embodiments, image processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. Image processor 14 may also be implemented by one or more special-purpose processing devices, such as an application specific integrated circuit (ASIC), a field programmable gate array (FPGA), a digital signal processor (DSP), a System on a Chip (SoC), or other suitable processors. As would be appreciated by those skilled in the art, in some embodiments, image processor 14 may be a special-purpose processor, rather than a general-purpose processor. Image processor 14 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Image processor 14 may also include graphical processing units, such as a GPU from the GeForce®, Quadro®, Tesla® family manufactured by Nvidia™, GMA, Iris™ family manufactured by Intel™, or the Radeon™ family manufactured by AMD™. Image processor 14 may also include accelerated processing units, such as the Desktop A-4(6,8) Series manufactured by AMD™, or the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein.

In addition, the term "processor" may include more than one processor, for example, a multi-core design, or a plurality of processors each having a multi-core design. Image processor 14 may be configured to execute sequences of computer program instructions, e.g., those stored in memory 16, to perform various operations, processes, and methods according to exemplary embodiments of the disclosure.

Memory 16 may store medical images 46. In some embodiments, medical images 46 may include, e.g., one or more MR image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), CT image (e.g., 2D CT, CBCT, 3D CT, 4D CT), ultrasound image (e.g., 2D ultrasound, 3D ultrasound, 4D ultrasound), PET image, X-ray image, fluoroscopic image, radiotherapy portal image, SPECT image, and/or computer-generated synthetic image (e.g., pseudo-CT images). Further, medical images 46 may include medical image data, for example, training images, ground truth images, and/or contoured images. Images stored in memory 16 may include registered and/or unregistered images, and the images may have been pre-processed or may be raw, unprocessed images. In some embodiments, medical images 46 may be received from image acquisition device 32. Accordingly, image acquisition device 32 may include an MR imaging device, a CT imaging device, a PET imaging device, an ultrasound imaging device, a fluoroscopic device, a SPECT imaging device, an integrated linac and MR imaging device, or other medical imaging devices for obtaining the medical images of the patient. Medical images 46 may be received and stored in any type of data or any type of format that image processing device 12 may use to perform operations consistent with the disclosed embodiments.

Memory 16 may be a non-transitory computer-readable medium, such as a read-only memory (ROM), a phase-change random access memory (PRAM), a static random access memory (SRAM), a flash memory, a random access memory (RAM), a dynamic random access memory (DRAM), such as synchronous DRAM (SDRAM), an electrically erasable programmable read-only memory (EEPROM), a static memory (e.g., flash memory, flash disk, static random access memory) or any other suitable type of random access memory, e.g., a cache, a register, a compact disc read-only memory (CD-ROM), a digital versatile disc (DVD) or other optical storage, a cassette tape, other magnetic storage device, or any other non-transitory medium that may be used to store information including images, data, or computer executable instructions (e.g., stored in any format) capable of being accessed by image processor 14, or any other type of computer device. The computer program instructions may be accessed by image processor 14, read from the ROM, or any other suitable memory location, and loaded into the RAM for execution by image processor 14.

For example, memory 16 may store one or more software applications. Software applications stored in memory 16 may include, for example, an operating system 43 for common computer systems, as well as for software-controlled devices. Further, memory 16 may store an entire software application, or only a part of a software application, that may be executable by image processor 14. For example, memory 16 may store one or more radiation therapy treatment plans 42.

Image processing device 12 may communicate with network 20 via communication interface 18, which may be communicatively coupled to image processor 14 and memory 16. Communication interface 18 may provide communication connections between image processing device 12 and radiotherapy system 10 components (e.g., permitting the exchange of data with external devices). For example, communication interface 18 may, in some embodiments, have appropriate interfacing circuitry to connect to user interface 36, which may be, e.g., a hardware keyboard, a keypad, and/or a touch screen through which a user may input information into radiotherapy system 10.

Communication interface 18 may include, for example, one or more of a network adaptor, a cable connector, a serial connector, a USB connector, a parallel connector, a high-speed data transmission adaptor (e.g., fiber, USB 3.0, thunderbolt), a wireless network adaptor (e.g., WiFi adaptor), a telecommunication adaptor (e.g., 3G, 4G/LTE), or other suitable interfaces. Communication interface 18 may include one or more digital and/or analog communication devices that may permit image processing device 12 to communicate with other machines and devices, such as remotely located components, via network 20.

Network 20 may provide the functionality of, for example, a local area network (LAN), a wireless network, a cloud computing environment (e.g., software as a service, platform as a service, infrastructure as a service, etc.), a client-server, or a wide area network (WAN). For example, network 20 may be a LAN or a WAN that may include other systems S1 (38), S2 (40), and S3 (41). Systems S1, S2, and S3 may be identical to image processing device 12 or may be different systems. In some embodiments, one or more systems in network 20 may form a distributed computing/simulation environment that may collaboratively perform the embodiments described herein. In some embodiments, one or more systems S1, S2, and S3 may include a CT scanner that obtains CT images (e.g., medical images 46). In addition, network 20 may be connected to Internet 22 to communicate with servers and clients that reside remotely on the Internet.

Therefore, network 20 may allow data transmission between image processing device 12 and a number of various other systems and devices, such as OIS 28, radiation therapy device 30, and/or image acquisition device 32. Further, data generated by the OIS 28 and/or image acquisition device 32 may be stored in memory 16, database 24, and/or hospital database 26. The data may be transmitted/received via network 20, through communication interface 18, in order to be accessed by image processor 14, as required.

Image processing device 12 may communicate with database 24 through network 20 to send/receive a plurality of various types of data stored on database 24. For example, database 24 may include machine data that comprises information associated with radiation therapy device 30, image acquisition device 32, and/or other machines and/or devices relevant to radiotherapy. Machine data information may include radiation beam size, arc placement, beam on and off time duration, control points, segments, MLC configuration, gantry speed, MRI pulse sequence, and/or other suitable information. Database 24 may be a storage device. One skilled in the art would appreciate that database 24 may include a plurality of devices located either in a central or a distributed manner.

In some embodiments, database 24 may include a processor-readable storage medium (not shown). While the processor-readable storage medium in some embodiments may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing and/or encoding a set of instructions for execution by a processor and that cause the processor to perform any one or more of the methodologies of the present disclosure. The term "processor-readable storage medium" shall accordingly be taken to include, but not be limited to, solid-state memories, optical, and magnetic media. For example, the processor-readable storage medium may be one or more volatile, non-transitory, or non-volatile tangible computer-readable media.

Image processor 14 may communicate with database 24 to read images into memory 16 and/or store images from memory 16 to database 24. For example, database 24 may be configured to store a plurality of images (e.g., 3D MRI, 4D MRI, 2D MRI slice images, CT images, 2D fluoroscopy images, X-ray images, raw data from MR scans or CT scans, Digital Imaging and Communications in Medicine (DIMCOM) data, etc.) that database 24 received from image acquisition device 32 or other image acquisition device. Database 24 may store data to be used by image processor 14 when executing software program 44, and/or when creating radiation therapy treatment plans 42. Image processing device 12 may receive medical images 46 (e.g., 2D MRI slice images, CT images, 2D fluoroscopy images, X-ray images, 3DMR images, 4D MR images, etc.) either from database 24, radiation therapy device 30 (e.g., a MRI-linac), and/or image acquisition device 32 to generate a treatment plan 42.

In an exemplary embodiment, radiotherapy system 100 may include an image acquisition device 32 configured to acquire medical images (e.g., MR images, such as 3D MRI, 2D streaming MRI, or 4D volumetric MRI, CT images, CBCT, PET images, functional MR images (e.g., fMRI, DCE-MRI, and diffusion MRI), X-ray images, fluoroscopic images, ultrasound images, radiotherapy portal images, SPECT images, etc.) of the patient. Image acquisition device 32 may, for example, be an MR imaging device, a CT imaging device, a PET imaging device, an ultrasound device, a fluoroscopic device, a SPECT imaging device, or any other suitable medical imaging device for obtaining one or more medical images of the patient. Images acquired by imaging acquisition device 32 may be stored within database 24 as either imaging data and/or test data. By way of example, the images acquired by imaging acquisition device 32 may be also stored by image processing device 12, as medical image data 46 in memory 16.

In some embodiments, for example, image acquisition device 32 may be integrated with radiation therapy device 30 as a single apparatus (e.g., an MRI device combined with a linac, also referred to as an "MRI-linac." Such an MRI-linac may be used, for example, to determine a location of a target organ or a target tumor in the patient, so as to direct radiation therapy accurately according to radiation therapy treatment plan 42 to a predetermined target.

Image acquisition device 32 may be configured to acquire one or more images of the patient's anatomy at a region of interest (e.g., a target organ, a target tumor, or both). Each image, typically a 2D image or slice, may include one or more parameters (e.g., a 2D slice thickness, an orientation, a location, etc.). In some embodiments, image acquisition device 32 may acquire a 2D slice in any orientation. For example, an orientation of the 2D slice may include a sagittal orientation, a coronal orientation, or an axial orientation. Image processor 14 may adjust one or more parameters, such as the thickness and/or orientation of the 2D slice, to include the target organ and/or target tumor. In an exemplary embodiment, 2D slices may be determined from information, such as a 3D MRI volume. Such 2D slices may be acquired by image acquisition device 32 in "real-time" while a patient is undergoing radiation therapy treatment, for example, when using radiation therapy device 30. "Real-time" may mean acquiring the data within milliseconds (e.g., 500 milliseconds or 300 milliseconds) or less.

Image processing device 12 may generate and store radiation therapy treatment plans 42 for one or more patients. Radiation therapy treatment plans 42 may provide information about a particular radiation dose to be applied to each patient. Radiation therapy treatment plans 42 may also include other radiotherapy information, such as beam angles, dose-histogram-volume information, the number of radiation beams to be used during therapy, the dose per beam, or other suitable information or combination thereof.

Image processor 14 may generate radiation therapy treatment plans 42 by using software programs 44, for example, treatment planning software, such as Monaco®, manufactured by Elekta AB of Stockholm, Sweden. In order to generate radiation therapy treatment plans 42, image processor 14 may communicate with image acquisition device 32 (e.g., a CT device, an MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, treatment planning device 110 may study the dose distribution not only in the target, but also in the OAR.

In order to delineate a target organ or a target tumor from the OAR, medical images, such as MR images, CT images, PET images, fMR images, X-ray images, ultrasound images, radiotherapy portal images, SPECT images, or other medical images, of the patient undergoing radiotherapy may be obtained by image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receive as low a radiation dose as possible). Other parameters that may be considered include the location of the target organ and the target tumor, the location of the OAR, and/or the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by an OAR proximate to the tumor (e.g., left and right parotid, optic nerves, eyes, lens, inner ears, spinal cord, brain stem, or other anatomy). After the radiation dose is determined for relevant anatomical structures (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and/or beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, image processing device 12 may generate a tailored radiation therapy treatment plan 42 having these parameters in order for radiation therapy device 30 to provide radiotherapy treatment to the patient.

In addition, radiotherapy system 10 may include a display device 34 and a user interface 36. Display device 34 may include one or more display screens configured to display medical images, interface information, treatment planning parameters (e.g., contours, dosages, beam angles, etc.) treatment plans, a target, localizing a target and/or tracking a target, or any suitable information to the user. User interface 36 may be a keyboard, a keypad, a touch screen, or any type of device that a user may input information to radiotherapy system 10. Alternatively, display device 34 and user interface 36 may be integrated into a device such as a smart phone, computer, or tablet computer, e.g., Apple iPad®, Lenovo Thinkpad®, Samsung Galaxy®, etc.

Furthermore, any and all components of radiotherapy system 10 may be implemented as a virtual machine (e.g., VMWare, Hyper-V, etc.). For example, a virtual machine may be software that functions as hardware. Therefore, a virtual machine may include at least one or more virtual processors, one or more virtual memories, and/or one or more virtual communication interfaces that together function as hardware. For example, image processing device 12, OIS 28, and/or image acquisition device 32 may be implemented as a virtual machine. Given the processing power, memory, and computational capability available, the entire radiotherapy system 10 may be implemented as a virtual machine.

Figure 2:
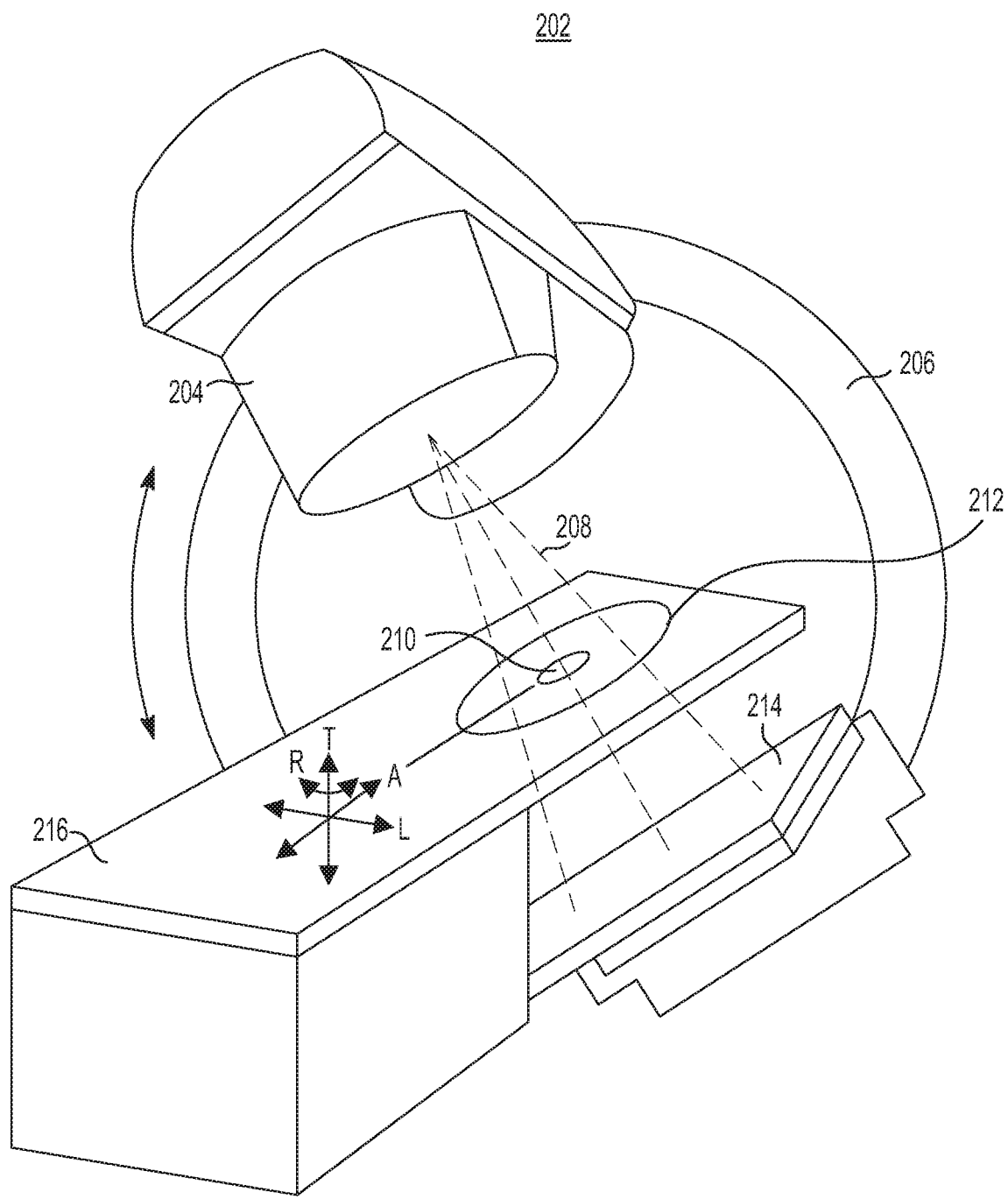
FIG. 2 illustrates an example of a radiation therapy system that may include a radiation therapy output configured to provide a therapy beam.

FIG. 2 illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as a multi-leaf collimator (MLC).

Referring back to FIG. 2, a patient may be positioned in a region 212, supported by the treatment couch 216 to receive a radiation therapy dose according to a radiation therapy treatment plan. The radiation therapy output 204 may be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 may be configured to rotate the therapy output 204 around an axis ("A"). Both the couch 216 and the radiation therapy output 204 may be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 may have an origin located at an isocenter 210. The isocenter 210 may be defined as a location where the central axis of the radiation therapy beam 208 intersects the origin of a coordinate axis, such as to deliver a prescribed radiation dose to a location on or within a patient. Alternatively, the isocenter 210 may be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 may be located within a field of the therapy beam 208.

The imaging detector 214 may be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 may be a flat panel detector (e.g., a direct detector or a scintillator detector). In this manner, the imaging detector 214 may be used to monitor the therapy beam 208 or the imaging detector 214 may be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 may be automatically positioned, and the therapy output 204 may establish the therapy beam 208 according to a specified dose for a particular therapy delivery instance. A sequence of therapy deliveries may be specified according to a radiation therapy treatment plan, such as using one or more different orientations or locations of the gantry 206, couch 216, or therapy output 204. The therapy deliveries may occur sequentially, but may intersect in a desired therapy locus on or within the patient, such as at the isocenter 210. A prescribed cumulative dose of radiation therapy may thereby be delivered to the therapy locus while damage to tissue nearby the therapy locus may be reduced or avoided.

Embodiments of the present disclosure may be configured to operate in conjunction with any suitable radiotherapy delivery system, for example, linacs and/or charged particle radiotherapy devices like those described above, or Cyber Knife technologies, or any suitable proton, carbon, ion, or photon radiotherapies. In the embodiments described herein, these technologies may be configured to provide motion tracking in addition to accounting for changes in shape of the target region.

Systems and Methods of Accounting for Changes in Shape

In current location tracking devices, a motion target volume is created to represent the volume of the tumor, and then movement of that motion target volume is tracked or otherwise accounted for during radiotherapy. The creation of a motion target volume, however, generally assumes that the tumor is rigid and does not account for changes in tumor shape. However, the 3D volume of a tumor may be a function of time, and a target region may in fact change shape prior to or during radiotherapy. For example, a tumor located near the bladder or digestive tract, or a tumor located near the lungs or diaphragm, may expand, be compressed, or otherwise undergo a shape change during or before radiotherapy, as a result of, e.g., natural body processes. Accordingly, the shape of the motion target volume created using known location tracking technology may provide an inaccurate representation of the target region by assuming that the target is rigid. This may be detrimental, because the entire target volume may need to be treated in order to effectively manage the disease.

Figure 3A:
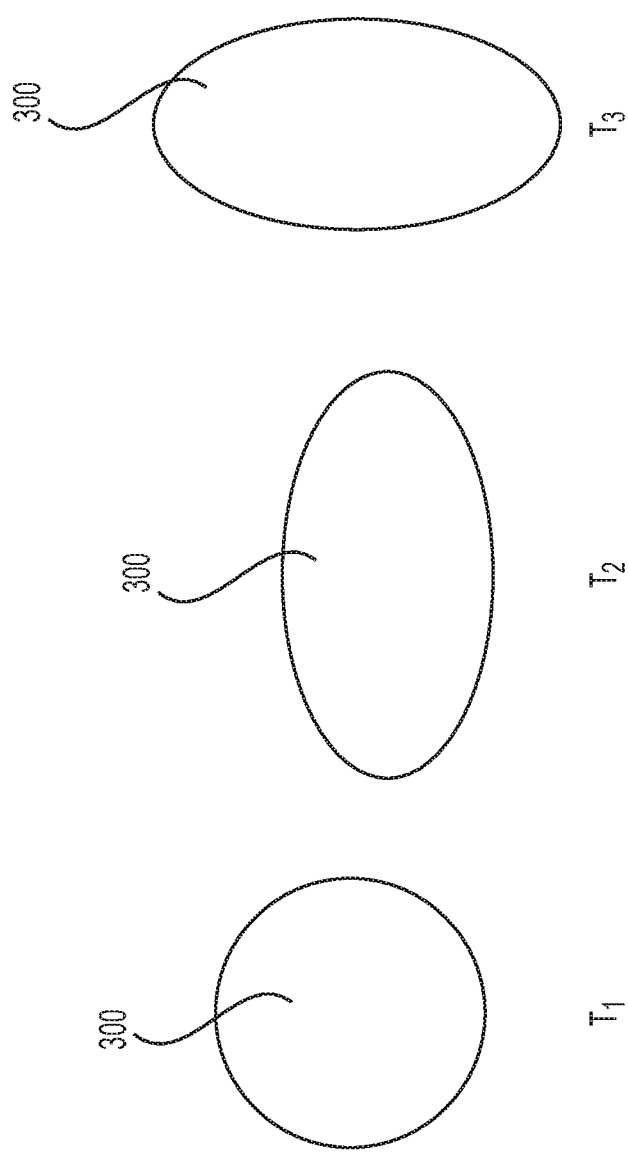
FIG. 3A schematically depicts an exemplary target region at various time points.

Embodiments of the present disclosure account for changes in tumor shape or configuration that may occur during and/or prior to radiotherapy. For example, FIG. 3A depicts the different shapes or configurations that a tumor 200 may take over the course of three different time points. At time $T_1$, tumor 200 may have a first shape, shown for purposes of simplification as a circle in FIG. 3A. In this exemplary embodiment, tumor 200 at time $T_1$ may have a non-deformed shape. At time $T_2$, tumor 200 may be subject to compression in a vertical direction, resulting in the wide ellipsoid shown at time $T_2$ in FIG. 3A. At time $T_3$, tumor 200 may be subject to compression in a horizontal direction, resulting in the ellipsoid shape shown at time $T_3$ in FIG. 3A. Accordingly, at each of the time points depicted, the shape and/or configuration of tumor 200 may vary.

Although tumor 200 is shown ranging in shape between a circle and two ellipsoids for the sake of simplicity, it is understood that tumor 200 may have more complex shapes and/or non-uniform shapes. Additionally, although tumor 200 is depicted in two dimensions, it is understood that tumor 200 may be three-dimensional. Different portions of tumor 200 or all of tumor 200 may change in shape, and these shape changes may be consistent or may vary across the tumor. For example, tumor 200 may bulge outwards in one region as another region of tumor 200 is compressed. The shape variations of the tumor may depend, at least in part, on the location of the tumor, orientation of the tumor, size of the tumor, density of the tumor, the type of tumor, or other characteristics or combinations of characteristics of the tumor.

To determine the variations in shape of tumor 200, imaging of tumor 200 at different time points may be taken. For example, during treatment planning, multiple images of tumor 200 may be captured. Exemplary imaging may include MR imaging, X-ray imaging, CT imaging, ultrasound imaging, PET, or fluoroscopy, among others. The imaging may then be analyzed to detect any changes in shape that tumor 200 may undergo in the various images. For example, analysis of the imaging may show that tumor 200 varies between the maximum deformations shown at times $T_1$ through $T_3$ of FIG. 3A. The images may then be processed in a number of different ways to generate a motion target volume that accounts for the changes in tumor shape.

Figure 3B:
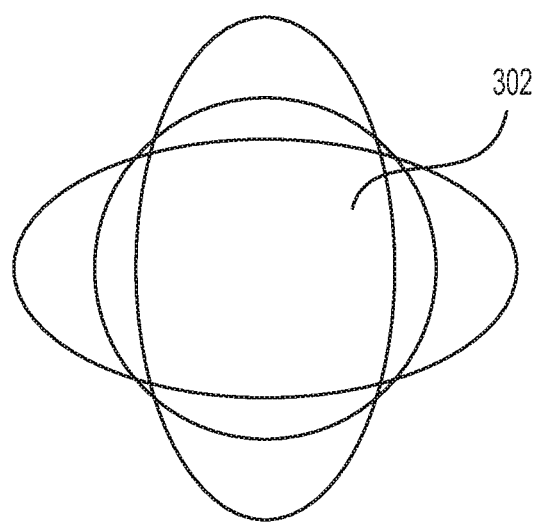
FIG. 3B schematically depicts a step in an exemplary method of the present disclosure taking into account the target region configurations of FIG. 3A.
Figure 3C:
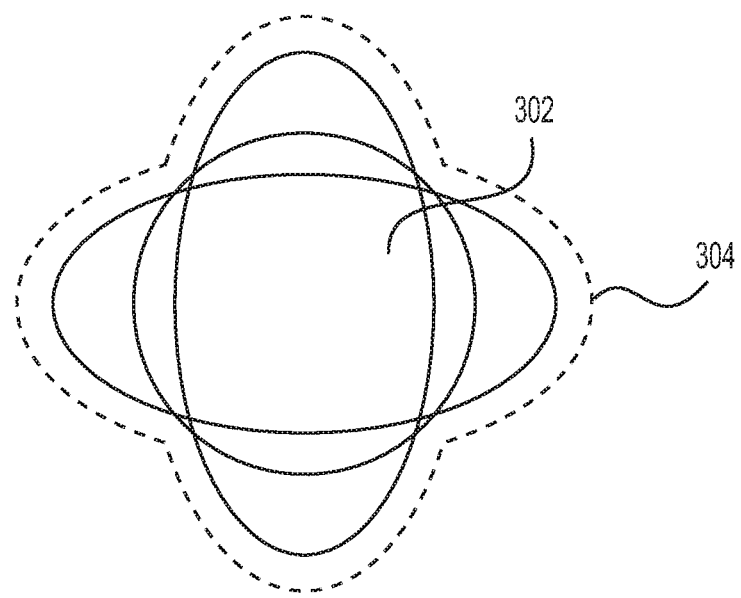
FIG. 3C schematically depicts a step in an exemplary method of the present disclosure taking into account the target region configurations of FIG. 3A.

The maximum shape deformations may be co-registered with one another. Co-registration is the process of finding the mathematical transformation that aligns multiple different radiographic images. In some aspects, the center of tumor 200 in each image may be used to align the images, as is shown in FIG. 3B. The outer-most perimeter of the overlapped shapes defines a target region 202 that accounts for changes in shape of tumor 200 during treatment. A margin 204 may be drawn around target region 202, as shown in FIG. 3C, to generate a target volume for use in treatment planning and radiotherapy. Margin 204 may be added, e.g., to account for sub-clinical disease spread that may not be completely detected by medical imaging (e.g., to create a CTV). In some aspects, another margin (not shown) may be drawn around margin 204 to account for uncertainty introduced during the treatment planning or delivery stages (e.g., to generate a PTV). In some aspects, however, no margin may be drawn, and target region 202 may be used to define the target volume.

Figure 4A:
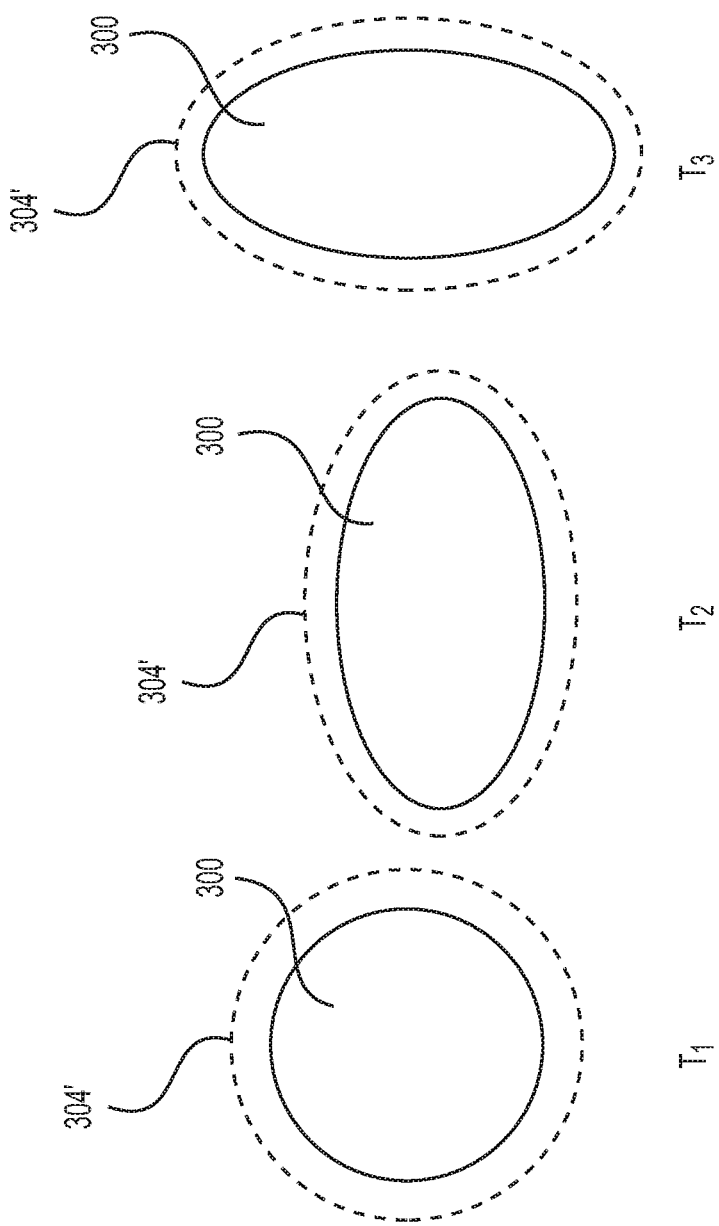
FIG. 4A schematically depicts a step in an exemplary method of the present disclosure taking into account the target region configurations of FIG. 3A.
Figure 4B:
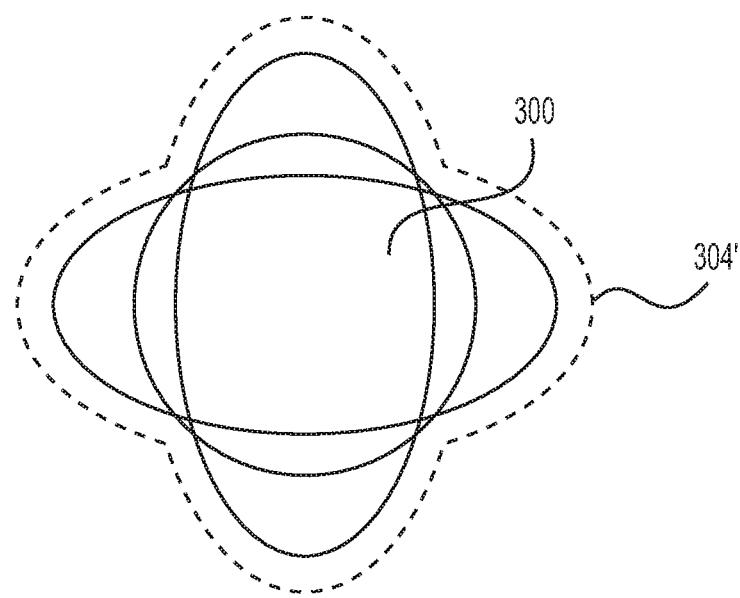
FIG. 4B schematically depicts a step in an exemplary method of the present disclosure taking into account the target region configurations of FIG. 3A.
Figure 5:
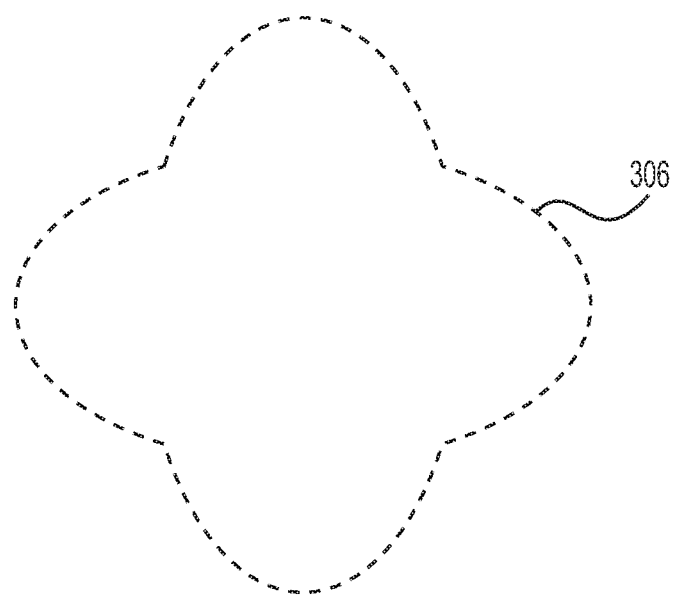
FIG. 5 schematically depicts a step in an exemplary method of the present disclosure taking into account the target region configurations of FIG. 3A.

In another aspect, margins 204' may be drawn around each tumor 200 shown in the medical imaging, or margins 204' may be drawn around each tumor 200 determined to represent a maximum extent of tumor shape deformation (as well as no deformation), as shown in FIG. 4A. The images of tumor 200 with their margins 204' may then be co-registered with one another, e.g., aligned at their centers, in order to define a target volume, as shown in FIG. 4B. The methods of FIGS. 3A-3C and 4A-4B may result in generation of a 3D motion target volume 206 (assuming non-zero margins are used), as shown in FIG. 5. If non-zero margins are used, then the motion target volume 206 may encompass the outermost contour of the overlapped tumor shapes from the plurality of images, as shown in FIG. 3B.

In an exemplary embodiment, a tumor may be located within or near a lung of a patient. Medical imaging may be used to capture the phases of the breathing cycle. For example, eight or ten or more phases of the respiratory cycle may be imaged. Each of the images of the tumor may be co-registered, either manually or automatically, and a shape that incorporates the shape of the tumor in all of the images may then be drawn around the co-registered image, similar to what is shown in FIG. 3C.

In some aspects, the target region may be located in a higher contrast region of the body, for example, the lungs or liver. In such embodiments, a maximum intensity projection (MIP) may be generated to determine the extent of the tumor in various directions as it changes shape. A MIP may be generated if the tumor appears white against a dark background on medical imaging, e.g., CT imaging. For example, with a high-contrast tumor, each of the images of the tumor taken at different time points (e.g., different phases of the respiratory cycle) may be co-registered, and the aggregate image may be analyzed on a voxel-by-voxel basis. Each voxel location may be analyzed to determine the maximum intensity value for that voxel location across each of the images. Once the maximum value at each voxel location is identified, the extent of the tumor shape may be determined. The high values at each voxel location represent the extent to which the tumor was present at that voxel, and, in the aggregate, the extent of the high-intensity values across voxels shows the extent of the tumor deformations in different directions as it changes shape.

In some aspects, a minimum intensity projection (MinIP) may be used if the target region appears dark against a white background on medical imaging, e.g. CT imaging. Each of the images of the tumor taken at different time points (e.g., different phases of the respiratory cycle) may be co-registered, and the aggregate image may be analyzed on a voxel-by-voxel basis. Each voxel location may be analyzed to determine the minimum intensity value for that voxel location among each of the images. Once the minimum value at each voxel location is identified, the extent of the tumor shape over time may be determined. The minimum values at each voxel location represent the maximum extent of the tumor at that voxel, and, in the aggregate, the extent of the low-intensity values across voxels shows the extent of the tumor in different directions as it changes shape.

In some aspects, co-registration may occur sequentially or may occur in parallel at one time. In some aspects, an operator may use a treatment planning system to select a series of images and automatically co-register the images. The calculated target volume data may be incorporated into a treatment plan and used to determine the appropriate location and dose of radiation based on the extent of where the tumor may be located over the course of its shape change during treatment. In some aspects, the shape of the beam delivered by a suitable radiotherapy treatment system may be adjusted to reflect the target volume of the tumor calculated to incorporate the extent of the shape change. The motion target volume may also be incorporated into a tumor tracking plan. By using the motion target volume as generated by embodiments of the present disclosure as the basis for tumor tracking, it may be possible to account for both tumor motion and changes in shape of the tumor.

Figure 6:
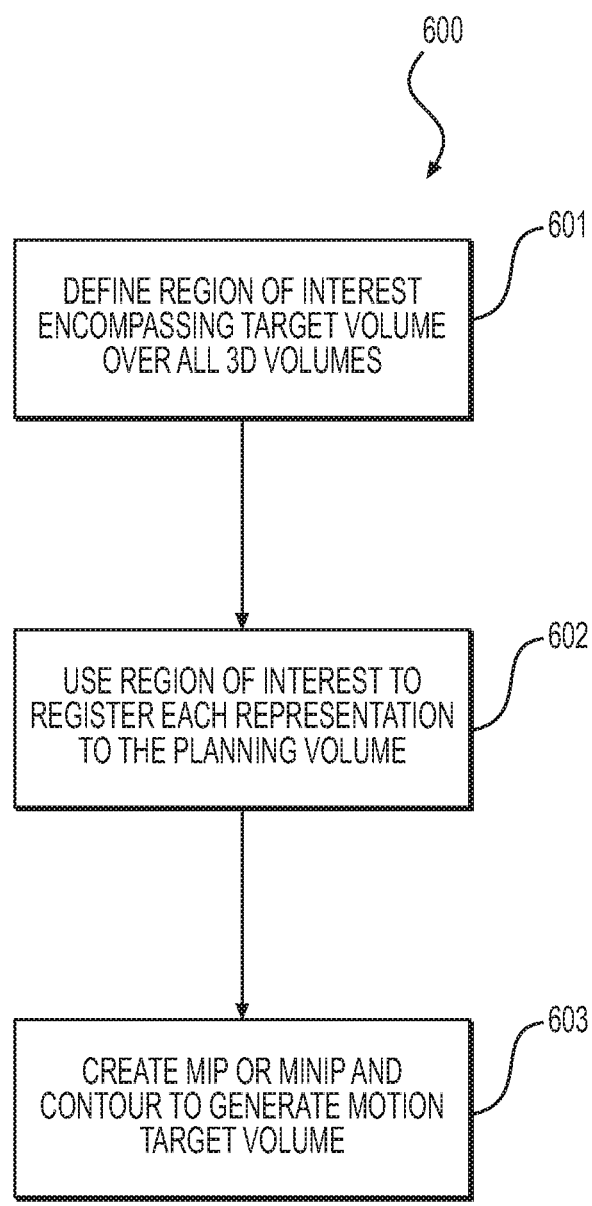
FIG. 6 is a flow chart depicting an exemplary method, in accordance with embodiments of the present disclosure.

Exemplary methods of the disclosure may be carried out in a number of different ways. A motion target volume may be generated according to any of the following methods. For example, according to the method 300 shown in FIG. 6, a region of interest may be defined that encompasses the target volume over all 3D volumes depicted in a plurality of images taken at different time points (301). This region of interest may be used to rigidly co-register each representation to the planning volume (302). A MIP or MinIP may then be created, and the MIP or MinIP may be manually or automatically contoured to generate a motion target volume (303).

Accordingly, a GTV may be drawn around the tumor in each of the plurality of images, and the images may be co-registered around the region of interest. This may result in a motion gross target volume (MGTV). A MIP or MinIP may then be created. A margin may then be added around the MGTV to obtain a motion clinical target volume (MCTV), and another margin may be added around the MCTV to generate a motion planning target volume (MPTV).

In some embodiments, a GTV and a CTV may be drawn around the tumor in each of the plurality of images, and the images may be co-registered. This may generate an MCTV. A margin may then be added around the MCTV to generate an MPTV. In other embodiments, a GTV, a CTV, and a PTV may be drawn around the tumor in each of the plurality of images, and the images may be co-registered. This may generate an MPTV.

Figure 7:
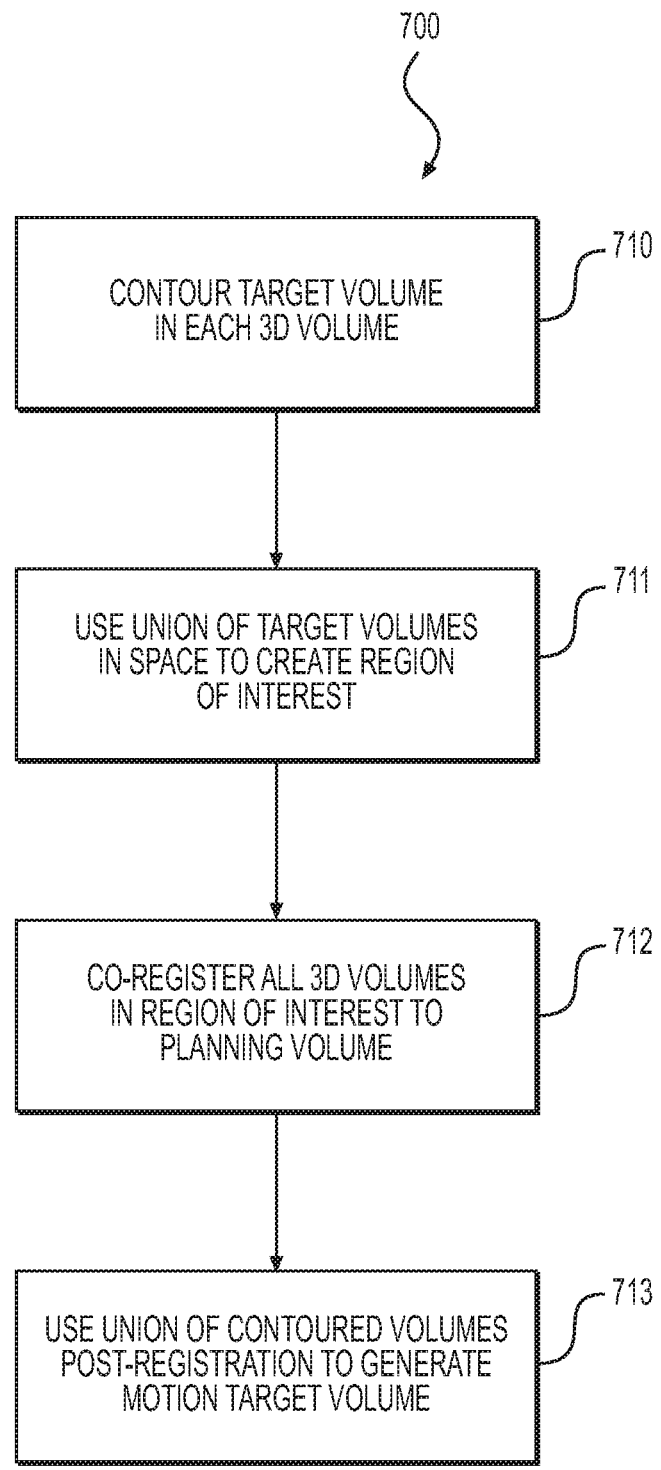
FIG. 7 is another flow chart depicting an exemplary method, in accordance with embodiments of the present disclosure.

In another aspect, shown as method 400 in FIG. 7, a target volume may be contoured for each 3D volume in each image (410). The union of the plurality of target volumes in space may then be used to create a region of interest (411). The 3D volumes in the region of interest may be rigidly co-registered to the planning volume (412). Then, the union of the contoured volumes post-registration may be used to generate the motion target volume (413).

Figure 8:
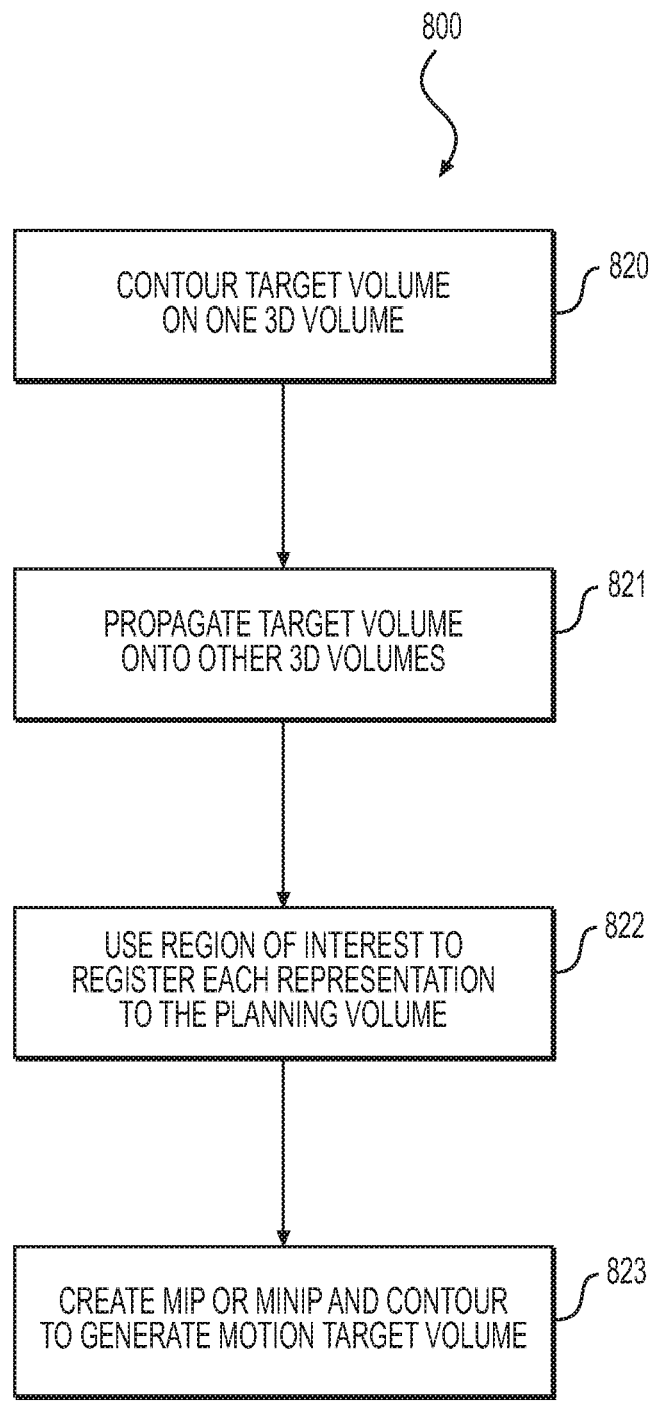
FIG. 8 is another flow chart depicting an exemplary method, in accordance with embodiments of the present disclosure.

In yet another aspect, shown in method 500 of FIG. 8, the target volume may be contoured on one 3D volume from one image (520). This target volume may then be propagated to other 3D volumes from other images, e.g., via standard auto-segmentation techniques (521). The region of interest generated through propagation to other 3D volumes may then be used to rigidly co-register each representation to the planning volume (522). A MIP or MinIP may next be created, and the MIP or MinIP may be manually or automatically contoured to generate a motion target volume (523).

Figure 9:
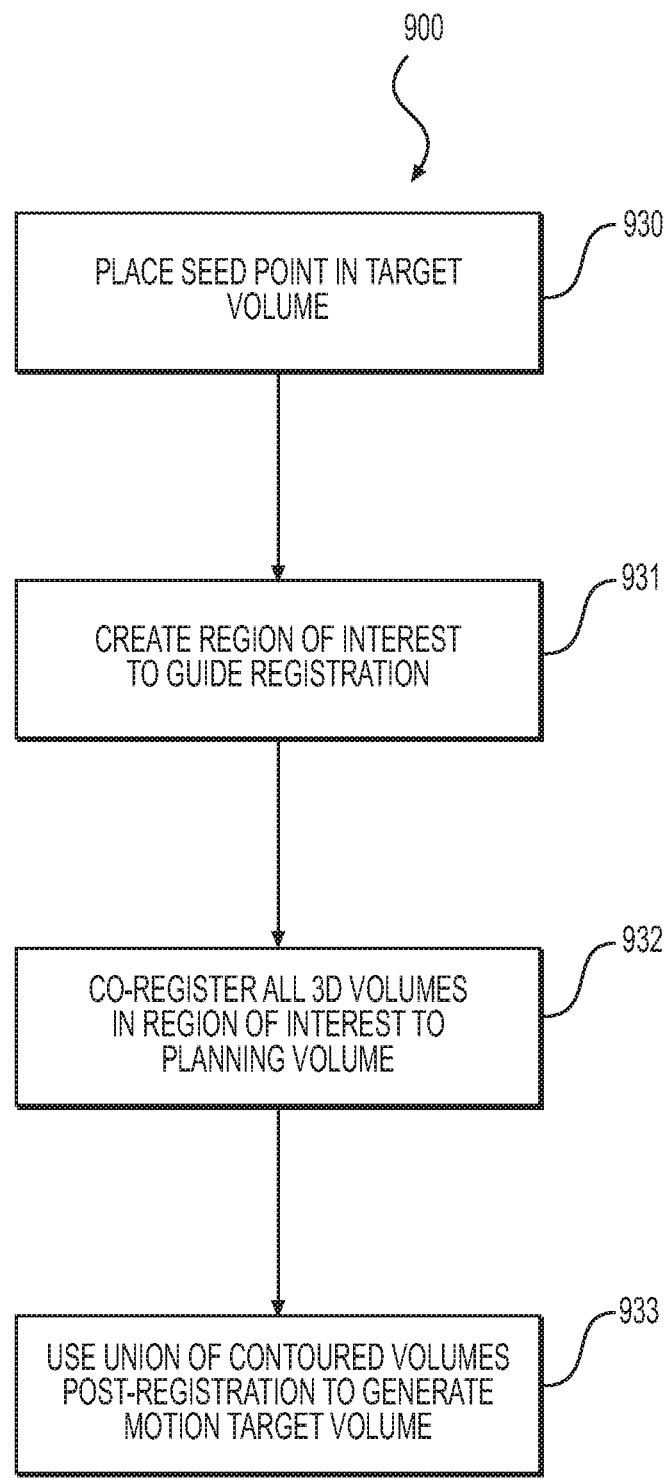
FIG. 9 is another flow chart depicting an exemplary method, in accordance with embodiments of the present disclosure.

In method 600 of FIG. 9, a seed point may be placed in a target volume (630), for example, drawn into a set of images manually by the user. A region of interest may then be created automatically to guide rigid co-registration (631). For example, a volume may be created around this seed point in a manner determined by the user, e.g., a sphere with a radius of 5 cm may be centered on the seed point, or a cube with 4 cm sides may be centered on the seed point. An edge-detection algorithm may be used to seek the edge of the target in each direction so that it automatically defines the volume and then adds a margin (which in some embodiments, may be a margin of 0 mm) to form a registration region of interest. The 3D volumes in the region of interest may be rigidly co-registered to the planning volume (632). Then, the union of the contoured volumes post-registration may be used to generate the motion target volume (633).

Figure 10:
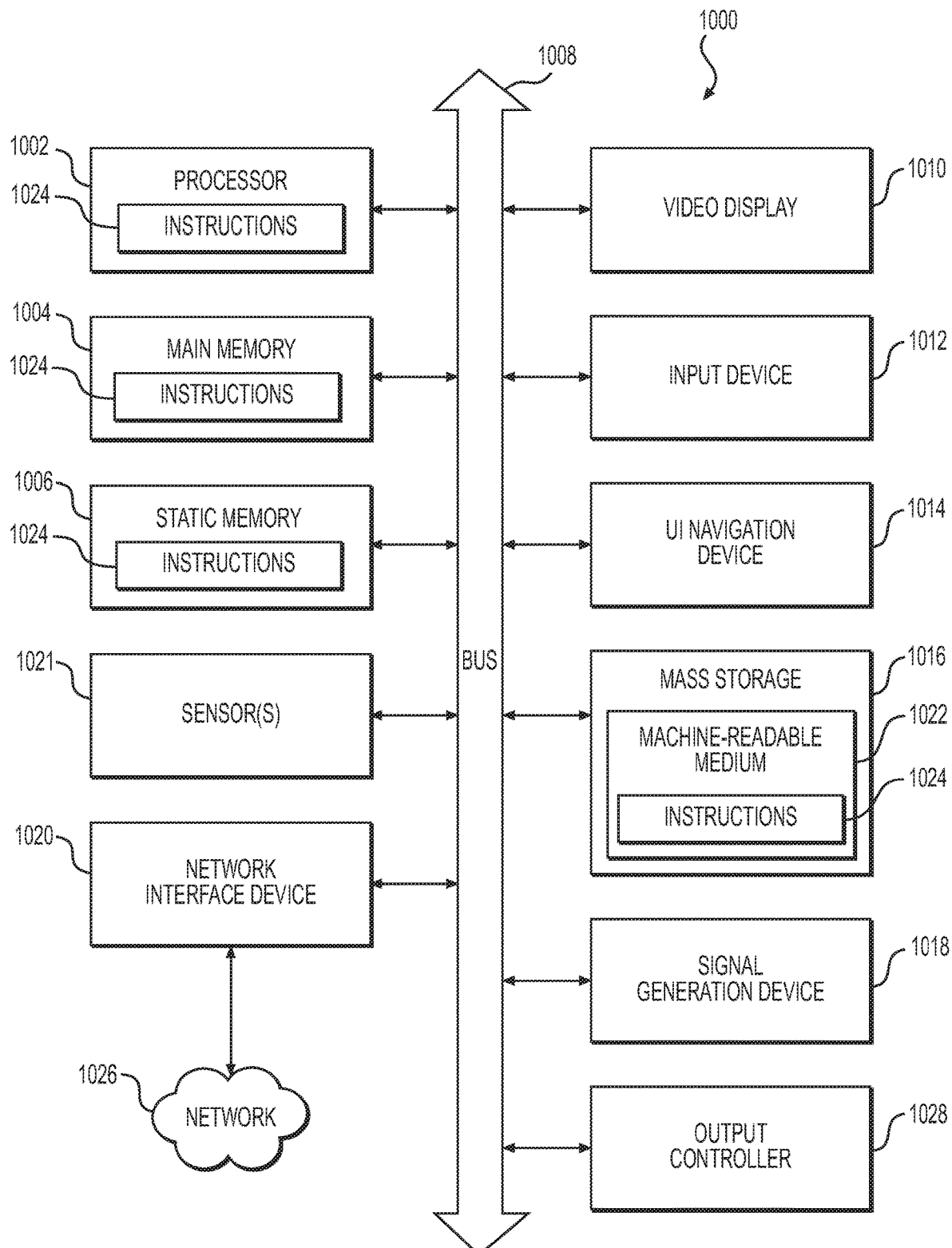
FIG. 10 illustrates a block diagram of an embodiment of a device or machine on which one or more of the methods as discussed herein may be implemented, e.g., to create a motion target volume for use with radiotherapy treatment planning and/or for use with tumor tracking for motion management.

FIG. 10 illustrates a block diagram of an embodiment of a system 1000 on which one or more of the methods as discussed herein may be implemented, such as to create a motion target volume for use with radiotherapy treatment planning and/or for use with tumor tracking for motion management. One or more items of the image processing device 112 may be implemented by the machine 1000. The machine 1000 may operate as a standalone device or may be connected (e.g., networked) to other machines. The image processing device 112 may include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 may include processing circuitry 1002 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. A datum or data associated with the described methods may be stored in or retrieved from such memory, and initialized or updated as desired to carry out the methods described herein. The machine 1000 (e.g., computer system) may further include a video display unit 1010 (e.g., a liquid crystal display (LCD) or a cathode ray tube (CRT)). The machine 1000 may also include an alphanumeric input device 1012 (e.g., a keyboard), a user interface (UI) navigation device 1014 (e.g., a mouse), a disk drive or mass storage unit 1016, a signal generation device 1018 (e.g., a speaker) and a network interface device 1020.

The disk drive unit 1016 may include a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated may include an output controller 1028. The output controller 1028 manages data flow to/from the machine 1000. The output controller 1028 may sometimes be called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A system for generating a motion target volume representative of changes in a shape of a target region within a body of a patient, the system comprising:
   at least one computer system configured to:
      receive a plurality of electronic medical images that include the target region within the body of the patient, wherein each of the plurality of images was taken at a different time point;
      define a three-dimensional volume containing the target region in each of the plurality of images, wherein the three-dimensional volume is different in at least two of the plurality of images because of a difference in shape of the target region in the at least two of the plurality of images;
      co-register the three-dimensional volumes; and
      generate the motion target volume, wherein the motion target volume encompasses each of the three-dimensional volumes.

2. The system of claim 1, wherein the co-registering occurs before the defining.

3. The system of claim 1, wherein the three-dimensional volume is a gross tumor volume.

4. The system of claim 1, wherein the at least one computer system is further configured to define a first margin around each of the three-dimensional volumes, wherein the first margin defines a clinical target volume.

5. The system of claim 4, wherein the at least one computer system is further configured to define a second margin around each of the first margins, wherein the second margin defines a planning target volume.

6. The system of claim 1, wherein the at least one computer system is further configured to define a first margin around the co-registered three-dimensional volumes, wherein the first margin defines a clinical target volume.

7. The system of claim 6, wherein the at least one computer system is further configured to define a second margin around the first margin, wherein the second margin defines a planning treatment volume.

8. The system of claim 1, wherein the plurality of images includes at least one of a magnetic resonance image or a computed tomography image.

9. The system of claim 1, wherein the co-registration comprises determining a mathematical transformation that aligns multiple images.

10. The system of claim 1, wherein the co-registration involves using an object centroid to align the images.

11. A computer-implemented method for generating a motion target volume representative of changes in shape of a target region within a body of a patient, the method comprising:
receiving a plurality of medical images that include the target region within the body of the patient, wherein each of the plurality of images was taken at a different time point;
contouring a three-dimensional target volume containing the target region in at least one of the plurality of images;
co-registering the plurality of images in a region around the three-dimensional target volume; and
generating the motion target volume, wherein the motion target volume encompasses a shape of the target region in each of the plurality of images.

12. The method of claim 11, wherein the contouring comprises contouring a three-dimensional target volume containing the target region in each of the plurality of images.

13. The method of claim 11, wherein contouring is performed on one of the plurality of images, and the method further comprises propagating the target volume from the one of the plurality of images onto the target region in another of the plurality of images.

14. The method of claim 11, further comprising creating a maximum intensity projection or a minimum intensity projection.

15. The method of claim 14, wherein a margin is added around the minimum intensity projection or the maximum intensity projection to create a clinical target volume.

16. The method of claim 15, wherein a margin is added around the clinical target volume to create a planning target volume.

17. The method of claim 11, wherein the contouring includes adding a margin around the three-dimensional volume, wherein the three-dimensional volume includes a tumor.

18. The method of claim 11, further comprising creating a region of interest to guide the co-registration.

19. A computer-implemented method for generating a motion target volume representative of changes in shape of a target region within a body of a patient of a patient, the method comprising:
receiving a plurality of medical images that include the target region within the body of the patient, wherein each of the plurality of images was taken at a different time point;
defining a region of interest for co-registration in at least one of the plurality of images;
co-registering the plurality of images in the region of interest; and
creating a maximum intensity projection or a minimum intensity projection for generation of the motion target volume.

20. The method of claim 19, wherein a region of interest for co-registration is defined in each of the plurality of images.

21. The method of claim 19, wherein the region of interest is a gross tumor volume.

22. The method of claim 19, further comprising adding a first margin around the maximum intensity projection or the minimum intensity projection.

23. The method of claim 22, wherein the first margin defines a clinical target volume.

24. The method of claim 23, further comprising adding a second margin around the clinical target volume, wherein the second margin defines a planning target volume.

* * * * *